United States Patent [19]

Abramovitz et al.

[11] Patent Number: 5,759,789
[45] Date of Patent: Jun. 2, 1998

[54] PROSTAGLANDIN RECEPTOR EP2

[75] Inventors: Mark Abramovitz, Dollard des Ormeaux; Mohammed Adam, Kirkland; Lison Bastien, St. Lazare; Richard Grygorczyk, Dollard des Ormeaux; Kathleen Metters, Montreal, all of Canada; Thomas H. Ruchmore, Hatfield, Pa.; Nicole Sawyer, Pincourt, Canada

[73] Assignee: Merck Frosst Canada, Inc., Kirkland, Canada

[21] Appl. No.: 586,897

[22] PCT Filed: Aug. 29, 1994

[86] PCT No.: PCT/CA94/00470

§ 371 Date: Aug. 5, 1996

§ 102(e) Date: Aug. 5, 1996

[87] PCT Pub. No.: WO95/06664

PCT Pub. Date: Mar. 9, 1995

Related U.S. Application Data

[63] Continuation-in-part of Ser. No. 115,365, Aug. 31, 1993, Pat. No. 5,605,814.

[51] Int. Cl.$^6$ .......................... C12Q 1/00; C07K 14/705; C12N 15/09
[52] U.S. Cl. .......................... 435/7.21; 435/69.1; 435/325; 530/350; 536/23.5
[58] Field of Search .......................... 530/350; 435/69.1, 435/325, 320.1, 252.3, 254.11, 7.1, 7.21; 536/23.5

[56] References Cited

FOREIGN PATENT DOCUMENTS 2090278   8/1993   Canada.

OTHER PUBLICATIONS

Breyer et al., J. of American Society of Nephrology, 5, 64P, 1994, Sep. 1994.
Honda et al., J. Biol. Chem., 268, 7759–7762, 1993, Apr. 1993.
Mestikawy et al., J. of Neurochemistry, 53, 1555–1566, 1989.
Watanabe et al., Biochimica et Biophysica Acta, 1074, 398–405, 1991.
R. Coleman, et al., Characterisation Of The Prostanoid Receptors Mediating Contraction of Guinea–Pig Isolated Trachea, (1985), Prostaglandins, 29, pp. 363–375.
P. Davies, et. al., Prostaglindins and Inflammation, (1992), Inflammation: Basic Principles And Clinical Correlates, Gallin, Goldstein, Snyderman, eds., 2nd Ed., pp. 123–138.
E. Horton, et al., Uterine Luteolytic Hormone: A Physiological Role for Prostaglandin F2a, (1976), Physiol. Rev., 56, pp. 595–651.
D. DeWitt, Prostaglandin endoperoxide synthase: regulation of enzyme expression, (1991), Biochim. Biophys, Acta, 1083, pp. 121–134.

J. Stjernschantz, et al., Phenyl substituted prostaglandin analogs for glaucoma treatment, (1992), Drugs Future, 17, pp. 691–704.
P. Racz, et al., Maintained Intraocular Pressure Reduction With Once–a–Day Application of a New Prostaglandin F2a Analogue (PhXA41), (1993), Arch. Opthalmol., 111, pp. 657–661.
J. Senior, et al., In vitro characterization of prostanoid FP–, DP–, IP–and TP–receptors on the non–pregnant human myometrium, (1992), Brit. J. Pharmacol., 107, pp. 215–221.
J. Senior, et al., In vitro characterization of prostanoid receptors on human myometrium at term pregnancy, (1993), Brit. J. Pharmacol., 108, pp. 501–506.
J. Csepli, et al., The Effect Of The Prostaglandin F2a Analogue ICI 81008 On Uterine Small Arteries And On Blood Pressure, (1975), Prostaglandins, 10, pp. 689–697.
R. Coleman, Methods in prostanoid receptor classification, (1987), Prostaglandins And Related Substances—A Practical Approach, IRL Press, 1st Ed., pp. 267–303.
R. Coleman, et al., A study of the prostanoid receptors mediating bronchocorstriction in the anaesthetized guinea–pig and dog, (1981), Brit. J. Pharmacol., 74, p. 913.
J. Barnard, et al., Evaluation of prostaglandin F2a and prostacyclin interactions in the isolated perfused rat lung, (1992), J. Appl. Physiol., 72, pp. 2469–2474.
J. Davis, et al., Prostaglandin F2a stimulates phosphatidylinositol 4,5–bisphosphate hydrolysis and mobilizes intracellular Ca2+ in bovine luteal cells, (1987), Proc. Natl. Acad. Sci. U.S.A., 84, pp. 3728–3732.
J. Kitanaka, et al., Astrocytes Possess Prostaglandin F2a Receptors Coupled To Phospholipase C, (1991), Biochem. Biophys. Res. Comm., 178, pp. 946–952.
F. Black, et al., Activation of inositol phospholipid breakdown by prostaglandin F2a without any stimulation of proliferation in quiescent NIH–3T3 fibroblasts, (1990), Biochem. Journal, 266, pp. 661–667.
A. Nakao, et al., Characterization of Prostaglandin F2a Receptor of Mouse 3T3 Fibroblasts and Its Functional Expression in Xenopus Laevis Oocytes, (1993), J. Cell Physiol., 155, pp. 257–264.
W. Powell, et al., Prostaglandin F2a Receptor in Ovine corpora lutea, (1974), Eur. J. Biochem., 41, pp. 103–107.
W. Powell, et al., Occurrence and Properties of a Prostaglandin F2a Receptor in Bovine Corpora Lutea, (1975), Eur. J. Biochem., 56, pp. 73–77.

(List continued on next page.)

*Primary Examiner*—Stephen Walsh
*Assistant Examiner*—Sally P. Teng
*Attorney, Agent, or Firm*—Joseph A. Coppola; Jack L. Tribble

[57] ABSTRACT

A novel prostaglandin receptor has been identified and DNA encoding the receptor has been isolated, purified, sequenced and expressed in host cells. This DNA encoding the novel prostaglandin receptor and host cells expressing the receptor are used to identify modulators of the prostaglandin receptor.

3 Claims, 7 Drawing Sheets

OTHER PUBLICATIONS

W. Powell, et al., Localization of a Prostaglandin F2a Receptor in Bovine Corpus luteum Plasma Membranes, (1976), Eur. J. Biochem., 61, pp. 605–611.

M. Molnar, et al., PGF2a and PGE2 binding to rat myometrium during gestation, parturition, and postpartum, (1990), Am. J. Physiol., 258, pp. E740–E747.

Th. Bauknecht, et al., Distribution of prostaglandin E2 and prostaglandin F2a receptors in human myometrium, (1981), Acta Endocrinol., 98, pp. 446–450.

F. Neuschafer–Rube, et al., Characterization of prostaglandin–F2a–binding sites on rat hepatocyte plasma membranes, (1993), Eur. J. Biochem., 211, pp. 163–169.

M. Hirata, et al., Cloning and expression of cDNA for a human thromboxane A2 receptor, (1991), Nature, 349, pp. 617–620.

Y. Sugimoto, et al., Two Isoforms of the EP3 Receptor with Different Carboxyl–terminal Domains, (1993), J. Biol. Chem., 268, pp. 2712–2718.

Y. Sugimoto, et al., Cloning and Expression of a cDNA for Mouse Prostaglandin E Receptor EP3 Subtype*, (1992), J. Biol. Chem., 267, pp. 6463–6466.

K. Bunce, et al., Differential Effects Of Prostaglandin On Unidirectional Absorption And Secretion in Rat Ileum, (1987), Gastroenterology, 92, p. 1332.

Y. Dong, et al., Prostaglandin E receptor subtypes in smooth muscle: agonist activities of stable prostacyclin analogues, (1986), Br. J. Pharmacol., 87, pp. 97–107.

B. Hedqvist, et al., Prostaglandin–Induced Neurotransmission Failure In The Field–Stimulated, Isolated Vas Deferens, (1972), Neuropharmacology, 11, pp. 177–187.

M. McKenniff, et al., Characterisation of receptors mediating the contractile effects of prostanoids in guinea–pig and human airways, (1988), Eur. J. Pharmacol., 153, pp. 149–159.

R. Eglen, et al., The action of prostanoid receptor agonists and antagonists on smooth muscle and platelets, (1988), Br. J. Pharmacol., 94, pp. 591–601.

J. Louttit, et al., Prostanoid EP–Receptors In Pig Saphenous Vein, (Jul. 26–31, 1992), 8th International Conf. on Prostaglandins, Abstract 258.

R. Lawrence, et al., Investigation of the prostaglandin E (EP–) receptor subtype mediating relaxation of the rabbit jugular vein, (1992), Br. J. Pharmacol., 105, pp. 817–824.

R. Coleman, et al., Prostanoids and their Receptors, (1989), Comprehensive Medicinal Chemistry, 3, pp. 643–714.

W. Campbell, et al., Lipid–Derived Autacoids: Eicosanoids And Platelet–Activating Factor, (1990), The Pharmacological Basis of Therapeutics, 8th Edition, pp. 600–617.

Masu, et al., "cDNA Cloning of Bovine Substance–K receptor through Oocyte Expression System", Nature, vol. 329, p. 836 (1987).

Loh, et al., "Characterization of prostaglandin E2 receptors expressed on human monocytic . . . ", Biochem Ciophys Acta, vol. 1177, No. 1, pp. 43–48 (May 8, 1993).

Namba, et al., "Mouse Throboxane A2 Receptor: cDNA Cloning, Expression and Northern Blot Analysis," Biochem and Biophys Res Comm., vol. 184, No. 3, pp. 1197–1203 (1992).

```
CGGCACAGCCTCACACCTGAACGCTGTCCTCCCGCAGACG
AGACCGGCGGGCACTGCAAAGCTGGGACTCGTCTTTGAAG
GAAAAAAATAGCGAGTAAGAAATCCAGCACCATTCTTCA
CTGACCCATCCCGCTGCACCTCTTGTTTCCCAAGTTTTTG
AAAGCTGGCAACTCTGACCTCGGTGTCCAAAAATCGACAG
CCACTGAGACCGGCTTTGAGAAGCCGAAGATTTGGCAGTT
TCCAGACTGAGCAGGACAAGGTGAAAGCAGGTTGGAGGCG
GGTCCAGGACATCTGAGGGCTGACCCTGGGGCTCGTGAG
GCTGCCACCGCTGCTGCCGCTACAGACCCAGCCTTGCACT
CCAAGGCTGCGCACCGCCAGCCACTATCATGTCCACTCCC
GGGGTCAATTCGTCCGCCTCCTTGAGCCCCGACCGGCTGA
ACAGCCAGTGACCATCCCGGCGGTGATGTTCATCTTCGG
GGTGGTGGGCAACCTGGTGGCCATCGTGGTGCTGTGCAAG
TCGCGCAAGGAGCAGAAGGAGACGACCTTCTACACGCTGG
TATGTGGGCTGGCTGTCACCGACCTGTTGGGCACTTTGTT
GGTGAGCCCGGTGACCATCGCCACGTACATGAAGGGCCAA
TGGCCCGGGGGCCAGCCGCTGTGCGAGTACAGCACCTTCA
TTCTGCTCTTCTTCAGCCTGTCCGGCCTCAGCATCATCTG
CGCCATGAGTGTCGAGCGCTACCTGGCCATCAACCATGCC
TATTTCTACAGCCACTACGTGGACAAGCGATTGGCGGGCC
TCACGCTCTTTGCAGTCTATGCGTCCAACGTGCTCTTTTG
CGCGCTGCCCAACATGGGTCTCGGTAGCTCGCGGCTGCAG
TACCCAGACACCTGGTGCTTCATCGACTGGACCACCAACG
TGACGGCGCACGCCGCCTACTCCTACATGTACGCGGGCTT
CAGCTCCTTCCTCATTCTCGCCACCGTCCTCTGCAACGTG
CTTGTGTGCGGCGCGCTGCTCCGCATGCACCGCCAGTTCA
TGCGCCGCACCTCGCTGGGCACCGAGCAGCACCACGCGGC
CGCGGCCGCCTCGGTTGCCTCCCGGGGCCACCCCGCTGCC
TCCCAGCCTTGCCGCGCCTCAGCGACTTTCGGCGCCGCC
GGAGCTTCCGCCGCATCGCGGGCGCCGAGATCCAGATGGT
```

FIG. 1A

```
CATCTTACTCATTGCCACCTCCCTGGTGGTGCTCATCTGC
TCCATCCCGCTCGTGGTGCGAGTATTCGTCAACCAGTTAT
ATCAGCCAAGTTTGGAGCGAGAAGTCAGTAAAAATCCAGA
TTTGCAGGCCATCCGAATTGCTTCTGTGAACCCCATCCTA
GACCCCTGGATATATATCCTCCTGAGAAAGACAGTGCTCA
GTAAAGCAATAGAGAAGATCAAATGCCTCTTCTGCCGCAT
TGGCGGGTCCCGCAGGGAGCGCTCCGGACAGCACTGCTCA
GACAGTCAAAGGACATCTTCTGCCATGTCAGGCCACTCTC
GCTCCTTCATCTCCGGGAGCTGAAGGAGATCAGCAGTAC
ATCTCAGACCCTCCTGCCAGACCTCTCACTGCCAGACCTC
AGTGAAAATGGCCTTGGAGGCAGGAATTTGCTTCCAGGTG
TGCCTGGCATGGGCCTGGCCCAGGAAGACACCACCTCACT
GAGGACTTTGCGAATATCAGAGACCTCAGACTCTTCACAG
GGTCAGGACTCAGAGAGTGTCTTACTGGTGGATGAGGCTG
GTGGGAGCGGCAGGGCTGGGCCTGCCCCTAAGGGGAGCTC
CCTGCAAGTCACATTTCCCAGTGAAACACTGAACTTATCA
GAAAAATGTATATAATAGGCAAGGAAAGAAATACAGTACT
GTTTCTGGACCCTTATAAAATCCTGTGCAATAGACACATA
CATGTCACATTTAGCTGTGCTCAGAAGGGCTATCATCA
(SEQ.ID.NO.: 1)
```

FIG. 1B

MSTPGVNSSASLSPDRLNSPVTIPAVMFIFGVVGNLVAIV
VLCKSRKEQKETTFYTLVCGLAVTDLLGTLLVSPVTIATY
MKGQWPGGQPLCEYSTFILLFFSLSGLSIICAMSVERYLA
INHAYFYSHYVDKRLAGLTLFAVYASNVLFCALPNMGLGS
SRLQYPDTWCFIDWTTNVTAHAAYSYMYAGFSSFLILATV
LCNVLVCGALLRMHRQFMRRTSLGTEQHHAAAAASVASRG
HPAASPALPRLSDFRRRRSFRRIAGAEIQMVILLIATSLV
VLICSIPLVVRVFVNQLYQPSLEREVSKNPDLQAIRIASV
NPILDPWIYILLRKTVLSKAIEKIKCLFCRIGGSRRERSG
QHCSDSQRTSSAMSGHSRSFISRELKEISSTSQTLLPDLS
LPDLSENGLGGRNLLPGVPGMGLAQEDTTSLRTLRISETS
DSSQGQDSESVLLVDEAGGSGRAGPAPKGSSLQVTFPSET
LNLSEKCI (SEQ.ID.NO.: 2)

FIG. 1C

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1958 base pairs
( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| CGGCACAGCC | TCACACCTGA | ACGCTGTCCT | CCCGCAGACG | AGACCGGCGG | GCACTGCAAA | 60 |
| GCTGGGACTC | GTCTTTGAAG | GAAAAAAAAT | AGCGAGTAAG | AAATCCAGCA | CCATTCTTCA | 120 |
| CTGACCCATC | CCGCTGCACC | TCTTGTTTCC | CAAGTTTTTG | AAAGCTGGCA | ACTCTGACCT | 180 |
| CGGTGTCCAA | AAATCGACAG | CCACTGAGAC | CGGCTTTGAG | AAGCCGAAGA | TTTGGCAGTT | 240 |
| TCCAGACTGA | GCAGGACAAG | GTGAAAGCAG | GTTGGAGGCG | GTCCAGGAC | ATCGAGGGC | 300 |
| TGACCCTGGG | GGCTCGTGAG | GCTGCCACCG | CTGCTGCCGC | TACAGACCCA | GCCTTGCACT | 360 |
| CCAAGGCTGC | GCACCGCCAG | CCACTATCAT | GTCCACTCCC | GGGGTCAATT | CGTCCGCCTC | 420 |
| CTTGAGCCCC | GACCGGCTGA | ACAGCCCAGT | GACCATCCCG | GCGGTGATGT | TCATCTTCGG | 480 |
| GGTGGTGGGC | AACCTGGTGG | CCATCGTGGT | GCTGTGCAAG | TCGCGCAAGG | AGCAGAAGGA | 540 |
| GACGACCTTC | TACACGCTGG | TATGTGGGCT | GGCTGTCACC | GACCTGTTGG | GCACTTTGTT | 600 |
| GGTGAGCCCG | GTGACCATCG | CCACGTACAT | GAAGGGCCAA | TGGCCCGGGG | GCCAGCCGCT | 660 |
| GTGCGAGTAC | AGCACCTTCA | TTCTGCTCTT | CTTCAGCCTG | TCCGGCCTCA | GCATCATCTG | 720 |
| CGCCATGAGT | GTCGAGCGCT | ACCTGGCCAT | CAACCATGCC | TATTTCTACA | GCCACTACGT | 780 |
| GGACAAGCGA | TTGGCGGGCC | TCACGCTCTT | TGCAGTCTAT | GCGTCCAACG | TGCTCTTTTG | 840 |
| CGCGCTGCCC | AACATGGGTC | TCGGTAGCTC | GCGGCTGCAG | TACCCAGACA | CCTGGTGCTT | 900 |
| CATCGACTGG | ACCACCAACG | TGACGGCGCA | CGCCGCCTAC | TCCTACATGT | ACGCGGGCTT | 960 |
| CAGCTCCTTC | CTCATTCTCG | CCACCGTCCT | CTGCAACGTG | CTTGTGTGCG | GCGCGCTGCT | 1020 |
| CCGCATGCAC | CGCCAGTTCA | TGCGCCGCAC | CTCGCTGGGC | ACCGAGCAGC | ACCACGCGGC | 1080 |
| CGCGGCCGCC | TCGGTTGCCT | CCCGGGGCCA | CCCCGCTGCC | TCCCAGCCT | TGCCGCGCCT | 1140 |
| CAGCGACTTT | CGGCGCCGCC | GGAGCTTCCG | CCGCATCGCG | GGCGCCGAGA | TCCAGATGGT | 1200 |
| CATCTTACTC | ATTGCCACCT | CCCTGGTGGT | GCTCATCTGC | TCCATCCCGC | TCGTGGTGCG | 1260 |
| AGTATTCGTC | AACCAGTTAT | ATCAGCCAAG | TTTGGAGCGA | GAAGTCAGTA | AAAATCCAGA | 1320 |
| TTTGCAGGCC | ATCCGAATTG | CTTCTGTGAA | CCCCATCCTA | GACCCCTGGA | TATATATCCT | 1380 |
| CCTGAGAAAG | ACAGTGCTCA | GTAAAGCAAT | AGAGAAGATC | AAATGCCTCT | TCTGCCGCAT | 1440 |
| TGGCGGGTCC | CGCAGGGAGC | GCTCCGGACA | GCACTGCTCA | GACAGTCAAA | GGACATCTTC | 1500 |
| TGCCATGTCA | GGCCACTCTC | GCTCCTTCAT | CTCCCGGGAG | CTGAAGGAGA | TCAGCAGTAC | 1560 |
| ATCTCAGACC | CTCCTGCCAG | ACCTCTCACT | GCCAGACCTC | AGTGAAAATG | GCCTTGGAGG | 1620 |
| CAGGAATTTG | CTTCCAGGTG | TGCCTGGCAT | GGGCCTGGCC | CAGGAAGACA | CCACCTCACT | 1680 |
| GAGGACTTTG | CGAATATCAG | AGACCTCAGA | CTCTTCACAG | GGTCAGGACT | CAGAGAGTGT | 1740 |
| CTTACTGGTG | GATGAGGCTG | GTGGGAGCGG | CAGGGCTGGG | CCTGCCCCTA | AGGGGAGCTC | 1800 |
| CCTGCAAGTC | ACATTTCCCA | GTGAAACACT | GAACTTATCA | GAAAAATGTA | TATAATAGGC | 1860 |
| AAGGAAAGAA | ATACAGTACT | GTTTCTGGAC | CCTTATAAAA | TCCTGTGCAA | TAGACACATA | 1920 |
| CATGTCACAT | TTAGCTGTGC | TCAGAAGGGC | TATCATCA | | | 1958 |

( 2 ) INFORMATION FOR SEQ ID NO:2:

( i ) SEQUENCE CHARACTERISTICS:
( A ) LENGTH: 488 amino acids
( B ) TYPE: amino acid
( C ) STRANDEDNESS: single ( D ) TOPOLOGY: linear ( i i ) MOLECULE TYPE: protein ( x i ) SEQUENCE DESCRIPTION: SEQ ID NO:2:

| Met<br>1 | Ser | Thr | Pro | Gly<br>5 | Val | Asn | Ser | Ser | Ala<br>10 | Ser | Leu | Ser | Pro | Asp<br>15 | Arg |
|---|---|---|---|---|---|---|---|---|---|---|---|---|---|---|---|
| Leu | Asn | Ser | Pro<br>20 | Val | Thr | Ile | Pro | Ala<br>25 | Val | Met | Phe | Ile | Phe<br>30 | Gly | Val |
| Val | Gly | Asn<br>35 | Leu | Val | Ala | Ile | Val<br>40 | Val | Leu | Cys | Lys | Ser<br>45 | Arg | Lys | Glu |
| Gln | Lys<br>50 | Glu | Thr | Thr | Phe | Tyr<br>55 | Thr | Leu | Val | Cys | Gly<br>60 | Leu | Ala | Val | Thr |
| Asp<br>65 | Leu | Leu | Gly | Thr<br>70 | Leu | Leu | Val | Ser | Pro<br>75 | Val | Thr | Ile | Ala | Thr<br>80 | Tyr |
| Met | Lys | Gly | Gln | Trp<br>85 | Pro | Gly | Gly | Gln | Pro<br>90 | Leu | Cys | Glu | Tyr | Ser<br>95 | Thr |
| Phe | Ile | Leu | Leu<br>100 | Phe | Phe | Ser | Leu | Ser<br>105 | Gly | Leu | Ser | Ile | Ile<br>110 | Cys | Ala |
| Met | Ser | Val<br>115 | Glu | Arg | Tyr | Leu | Ala<br>120 | Ile | Asn | His | Ala | Tyr<br>125 | Phe | Tyr | Ser |
| His | Tyr<br>130 | Val | Asp | Lys | Arg | Leu<br>135 | Ala | Gly | Leu | Thr | Leu<br>140 | Phe | Ala | Val | Tyr |
| Ala<br>145 | Ser | Asn | Val | Leu | Phe<br>150 | Cys | Ala | Leu | Pro | Asn<br>155 | Met | Gly | Leu | Gly | Ser<br>160 |
| Ser | Arg | Leu | Gln | Tyr<br>165 | Pro | Asp | Thr | Trp | Cys<br>170 | Phe | Ile | Asp | Trp | Thr<br>175 | Thr |
| Asn | Val | Thr | Ala<br>180 | His | Ala | Ala | Tyr | Ser<br>185 | Tyr | Met | Tyr | Ala | Gly<br>190 | Phe | Ser |
| Ser | Phe | Leu<br>195 | Ile | Leu | Ala | Thr | Val<br>200 | Leu | Cys | Asn | Val | Leu<br>205 | Val | Cys | Gly |
| Ala | Leu<br>210 | Leu | Arg | Met | His | Arg<br>215 | Gln | Phe | Met | Arg | Arg<br>220 | Thr | Ser | Leu | Gly |
| Thr<br>225 | Glu | Gln | His | His | Ala<br>230 | Ala | Ala | Ala | Ala | Ser<br>235 | Val | Ala | Ser | Arg<br>240 | Gly |
| His | Pro | Ala | Ala | Ser<br>245 | Pro | Ala | Leu | Pro | Arg<br>250 | Leu | Ser | Asp | Phe | Arg<br>255 | Arg |
| Arg | Arg | Ser | Phe<br>260 | Arg | Arg | Ile | Ala | Gly<br>265 | Ala | Glu | Ile | Gln | Met<br>270 | Val | Ile |
| Leu | Leu | Ile<br>275 | Ala | Thr | Ser | Leu | Val<br>280 | Val | Leu | Ile | Cys | Ser<br>285 | Ile | Pro | Leu |
| Val<br>290 | Val | Arg | Val | Phe | Val<br>295 | Asn | Gln | Leu | Tyr | Gln<br>300 | Pro | Ser | Leu | Glu | Arg |
| Glu<br>305 | Val | Ser | Lys | Asn | Pro<br>310 | Asp | Leu | Gln | Ala | Ile<br>315 | Arg | Ile | Ala | Ser | Val<br>320 |
| Asn | Pro | Ile | Leu | Asp<br>325 | Pro | Trp | Ile | Tyr | Ile<br>330 | Leu | Leu | Arg | Lys | Thr<br>335 | Val |
| Leu | Ser | Lys | Ala<br>340 | Ile | Glu | Lys | Ile | Lys<br>345 | Cys | Leu | Phe | Cys | Arg<br>350 | Ile | Gly |
| Gly | Ser | Arg<br>355 | Arg | Glu | Arg | Ser | Gly<br>360 | Gln | His | Cys | Ser | Asp<br>365 | Ser | Gln | Arg |
| Thr | Ser<br>370 | Ser | Ala | Met | Ser<br>375 | Gly | His | Ser | Arg | Ser<br>380 | Phe | Ile | Ser | Arg | Glu |
| Leu<br>385 | Lys | Glu | Ile | Ser | Ser<br>390 | Thr | Ser | Gln | Thr | Leu<br>395 | Leu | Pro | Asp | Leu | Ser<br>400 |

| | | | | | | | | | | | | | | |
|---|---|---|---|---|---|---|---|---|---|---|---|---|---|---|
| Leu | Pro | Asp | Leu | Ser 405 | Glu | Asn | Gly | Leu | Gly 410 | Gly | Arg | Asn | Leu | Leu 415 | Pro |
| Gly | Val | Pro | Gly 420 | Met | Gly | Leu | Ala | Gln 425 | Glu | Asp | Thr | Thr | Ser 430 | Leu | Arg |
| Thr | Leu | Arg 435 | Ile | Ser | Glu | Thr | Ser 440 | Asp | Ser | Ser | Gln | Gly 445 | Gln | Asp | Ser |
| Glu | Ser 450 | Val | Leu | Leu | Val | Asp 455 | Glu | Ala | Gly | Gly | Ser 460 | Gly | Arg | Ala | Gly |
| Pro 465 | Ala | Pro | Lys | Gly | Ser 470 | Ser | Leu | Gln | Val | Thr 475 | Phe | Pro | Ser | Glu | Thr 480 |
| Leu | Asn | Leu | Ser | Glu 485 | Lys | Cys | Ile | | | | | | | | |

PROSTAGLANDIN RECEPTOR EP2

This application is the U.S. national phase (35 U.S.C. §371) of International Patent Application No. PCT/CA94/00470, filed Aug. 29, 1994, which is a continuation-in-part of U.S. patent application Ser. No. 08/115,365, filed Aug. 31, 1993, now U.S. Pat. No. 5,605,814.

BACKGROUND OF THE INVENTION

The physiological actions of prostaglandin (PG)$E_2$ are mediated through interaction with the prostaglandin E receptor(s). There are three subtypes of the EP receptor, $EP_1$, EP2 and $EP_3$ (for review see Coleman et al., 1989). These three subtypes all show high affinity for PGE2 but show differences in their affinities for various agonists and antagonists and exert their actions through different secondary transduction mechanisms. Thus activation of the EP1 receptor is associated with a rise in IP3 and intracellular calcium, activation of the EP2 receptor results in a rise in intracellular cyclic AMP and activation of the EP3 receptor a fall in intracellular cyclic AMP. To date the only members of this family to be cloned are the mouse EP2 (Honda et al., 1993) and the mouse $EP_{3\alpha}$ and $EP_{3\beta}$ (Sugimoto et al., 1992; Sugimoto et al., 1993) subtypes. EP2 receptors are normally found on a wide variety of cells including the small intestine, kidney, stomach, muscle, eye, uterus, thymus and trachea, in humans and other animals. Binding of prostaglandin $E_2$ to the EP2 receptor protein elicits an increase in intracellular cAMP levels. This signal causes the tissues to respond, for example, by smooth muscle relaxation.

Functional activities of the EP2 receptor have been studied using tissue preparations such as guinea-pig ileum circular muscle, cat trachea, guinea-pig trachea and cell preparations, such as lymphocytes and osteoclasts. The above methods for studying EP2 receptor activities have several disadvantages in that they require preparations containing several different but related receptor populations, with different ligand binding properties making measurements of absolute potency and selectivity very difficult. In addition, tissues contain very low levels of EP2 receptor and since tissue samples are required, compounds cannot satisfactorily be tested as effectors of the human EP2 receptor.

SUMMARY OF THE INVENTION

A novel prostaglandin receptor protein termed EP2 has been isolated and purified from human cells. A DNA molecule encoding the full length EP2 protein has been isolated and purified, and the nucleotide sequence has been determined. The EP2 encoding DNA has been cloned into expression vectors and these expression vectors, when introduced into recombinant host cells, cause the recombinant host cells to express a functional EP2 receptor protein. The novel EP2 protein, the EP2-encoding DNA, the expression vectors and recombinant host cells expressing recombinant EP2 are useful in the identification of modulators of EP2 receptor activity.

A method of identifying EP2 receptor modulators is also disclosed which utilizes the recombinant EP2 expressing host cells. Modulators of EP2 activity are useful for the treatment of prostaglandin-related diseases and for modulating the effects of prostaglandins on the EP2 receptor.

BRIEF DESCRIPTION OF THE DRAWINGS

FIGS. 1A–C—The complete DNA sequence encoding the EP2 receptor protein is shown above the complete deduced amino acid sequence of the EP2 receptor protein.

DETAILED DESCRIPTION OF THE INVENTION

Figure 2:
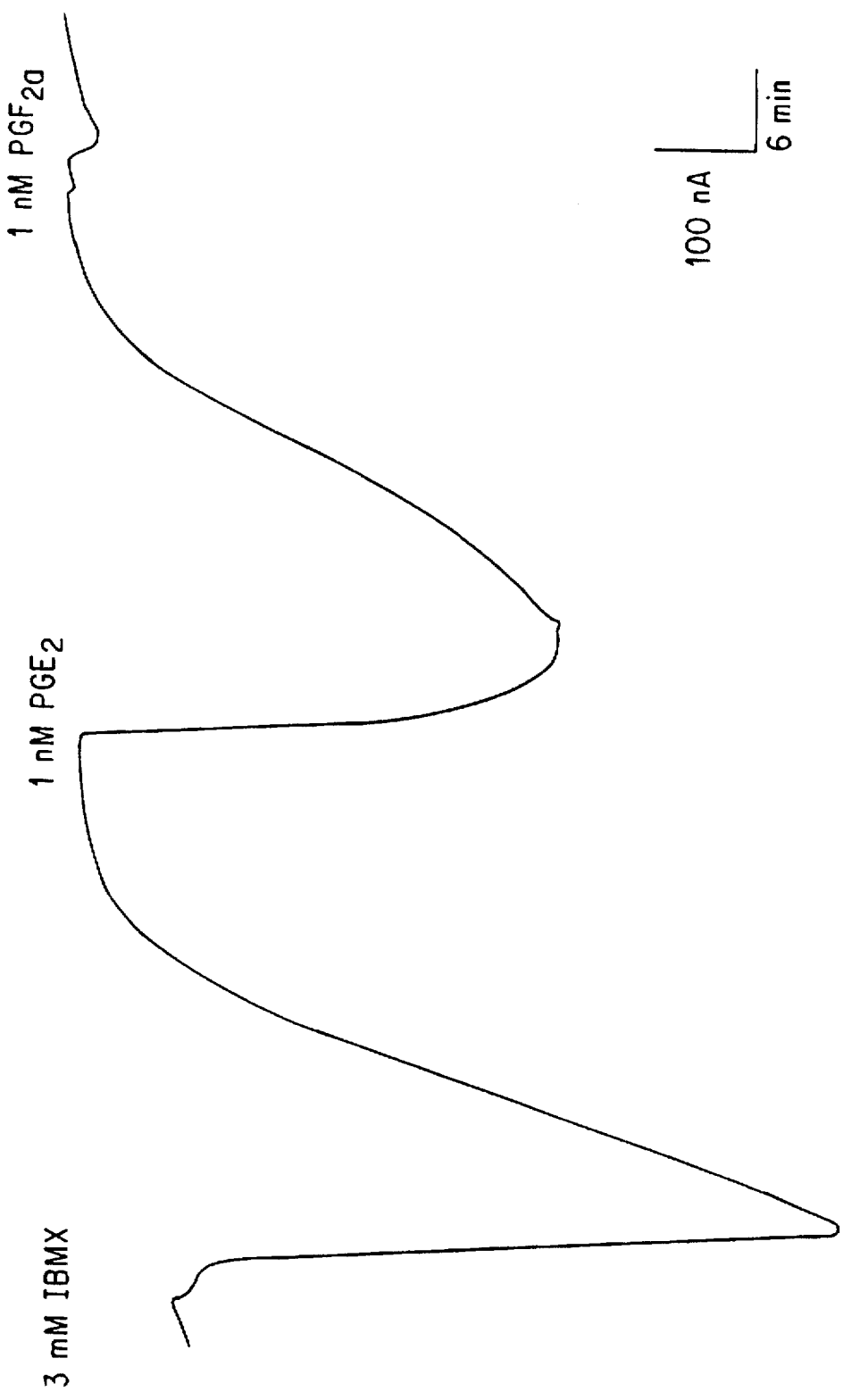
FIG. 2—Expression of the prostaglandin E2 receptor in EP2 cDNA-injected Xenopus oocytes is shown by an inward cAMP-dependent $Cl^-$ current (shown as downward deflection) evoked by bath perfusion of 1 nM PGE2 when the oocyte was injected with 1.6 ng EP2 cDNA plus 2.5 ng CFTR cDNA and voltage-clamped at −60 mV.

The present invention relates to cDNA encoding a novel prostaglandin receptor, termed EP2. The present invention is also related to recombinant host cells which express the cloned EP2-encoding DNA contained in a recombinant expression plasmid. The present invention is also related to methods for the screening of substances which modulate EP2 receptor activity. The DNA of the present invention is isolated from EP2 producing cells. EP2, as used herein, refers to a G protein-coupled receptor which can specifically bind prostaglandin molecules.

Mammalian cells capable of producing EP2 include, but are not limited to, cells derived from small intestine, kidney, stomach, vascular smooth muscle, eye, placenta, uterus, lyphocytes, osteoclasts and the tracheobronchial tree. Transformed mammalian cell lines which produce EP2 include, but are not limited to, mastocytoma P-815 cells. The preferred cells for the present invention include normal human kidney and lung cells and the most preferred cells are human thymus cells.

Other cells and cell lines may also be suitable for use to isolate EP2 cDNA. Selection of suitable cells may be done by screening for EP2 on cell surfaces. Methods for detecting EP2 activity are well known in the art and measure the binding of radiolabelled ligand specific for the receptor. Cells which possess EP2 activity in this assay may be suitable for the isolation of EP2 cDNA.

Any of a variety of procedures may be used to clone EP2 cDNA. These methods include, but are not limited to, direct functional expression of the EP2 cDNA following the construction of an EP2-containing cDNA library in an appropriate expression vector system. Another method is to screen an EP2-containing cDNA library constructed in a bacteriophage or plasmid shuttle vector with a labelled oligonucleotide probe designed from the amino acid sequence of the EP2 protein. The preferred method consists of screening an EP2-containing cDNA library constructed in a bacteriophage or plasmid shuttle vector with a partial cDNA encoding the EP2 protein. This partial cDNA is obtained by the specific PCR amplification of EP2 DNA fragments through the design of degenerate oligonucleotide primers from the amino acid sequence known for other G protein-coupled receptors which are related to the prostaglandin EP2 receptors.

It is readily apparent that other types of libraries, as well as libraries constructed from other cells or cell types, may be useful for isolating EP2-encoding DNA. Other types of libraries include, but are not limited to, cDNA libraries derived from other cells or cell lines and genomic DNA libraries.

It is readily apparent that suitable cDNA libraries may be prepared from cells or cell lines which have EP2 activity. The selection of cells or cell lines for use in preparing a cDNA library to isolate EP2 cDNA may be done by first measuring cell associated EP2 activity using the known labelled ligand binding assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, New York, 1982).

It is also readily apparent that DNA encoding EP2 may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, New York, 1982).

In order to clone the EP2 gene by one of the preferred methods, the amino acid sequence or DNA sequence of EP2 or a homologous protein is necessary. To accomplish this, EP2 protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial EP2 DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the EP2 sequence but others in the set will be capable of hybridizing to EP2 DNA even in the presence of DNA oligonucleotides with mismatches. The mismatched DNA oligonucleotides may still sufficiently hybridize to the EP2 DNA to permit identification and isolation of EP2 encoding DNA.

Using one of the preferred methods, cDNA clones encoding EP2 are isolated in a two-stage approach employing polymerase chain reaction (PCR) based technology and cDNA library screening. In the first stage, $NH_2$-terminal and internal amino acid sequence information from the purified EP2 or a homologous protein is used to design degenerate oligonucleotide primers for the amplification of EP2-specific DNA fragments. In the second stage, these fragments are cloned to serve as probes for the isolation of full length cDNA from cDNA libraries.

The sequence for the near full-length cDNA encoding EP2 is shown in Table 1, and was designated clone EP2. The deduced amino acid sequence of EP2 from the cloned cDNA is shown in Table 2. Inspection of the determined cDNA sequence reveals the presence of a single, large open reading frame that encodes for a protein of approximately 488 amino acids.

The cloned EP2 cDNA obtained through the methods described above may be recombinantly expressed by molecular cloning into an expression vector containing a suitable promoter and other appropriate transcription regulatory elements, and transferred into prokaryotic or eukaryotic host cells to produce recombinant EP2. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant EP2 in mammalian cells. Commercially available mammalian expression vectors which may be suitable for recombinant EP2 expression, include but are not limited to, pMClneo (Stratagene), pXT1 (Stratagene), pSG5 (Stratagene), pcDNAI, pcDNAIamp (Invitrogen), EBO-pSV2-neo (ATCC 37593) pBPV-1(8-2) (ATCC 37110), pdBPV-MMTneo(342-12) (ATCC 37224), pRS-Vgpt (ATCC 37199), pRSVneo (ATCC 37198), pSV2-dhfr (ATCC 37146), pUCTag (ATCC 37460), 1ZD35 (ATCC 37565), and vaccinia virus transfer vector pTM1.

DNA encoding EP2 may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, infection, protoplast fusion, and electroporation. The expression vector-containing cells are individually analyzed to determine whether they produce EP2 protein. Identification of EP2 expressing cells may be done by several means, including but not limited to immunological reactivity with anti-EP2 antibodies, and the presence of host cell-associated EP2 activity.

Expression of EP2 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the EP2 cDNA sequence(s) that yields optimal levels of receptor activity and/or EP2 protein, EP2 cDNA molecules including but not limited to the following can be constructed: the full-length open reading frame of the EP2 cDNA and various constructs containing portions of the cDNA encoding only specific domains of the receptor protein or rearranged domains of the protein. All constructs can be designed to contain none, all or portions of the 5' and/or 3' untranslated region of EP2 cDNA. EP2 activity and levels of protein expression can be determined following the introduction, both singly and in combination, of these constructs into appropriate host cells. Following determination of the EP2 cDNA cassette yielding optimal expression in transient assays, this EP2 cDNA construct is transferred to a variety of expression vectors (including recombinant viruses), including but not limited to those for mammalian cells, plant cells, insect cells, oocytes, E. coli, and yeast cells.

Mammalian cell transfectants are assayed for both the levels of EP2 receptor activity and levels of EP2 protein by the following methods. Assessing EP2 receptor activity involves the direct introduction of a labelled ligand to the cells and determining the amount of specific binding of the ligand to the EP2-expressing cells. Binding assays for receptor activity are known in the art (Frey et al., 1993, Eur. J. Pharmacol., 244, pp 239–250).

Levels of EP2 protein in host cells is quantitated by a variety of techniques including, but not limited to, immunoaffinity and/or ligand affinity techniques. EP2-specific affinity beads or EP2-specific antibodies are used to isolate $^{35}$S-methionine labelled or unlabelled EP2 protein. Labelled EP2 protein is analyzed by SDS-PAGE. Unlabelled EP2 protein is detected by Western blotting, ELISA or RIA assays employing EP2 specific antibodies.

Following expression of EP2 in a host cell, EP2 protein may be recovered to provide EP2 in active form, capable of binding EP2-specific ligands. Several EP2 purification procedures are available and suitable for use. Recombinant EP2 may be purified from cell membranes by various combinations of, or individual application of standard separation techniques including but not limited to detergent solubilization, salt fractionation, ion exchange chromatography, size exclusion chromatography, hydroxylapatite adsorption chromatography and hydrophobic interaction chromatography.

In addition, recombinant EP2 can be separated from other cellular proteins by use of an immuno-affinity column made with monoclonal or polyclonal antibodies specific for full length nascent EP2, or polypeptide fragments of EP2.

Monospecific antibodies to EP2 are purified from mammalian antisera containing antibodies reactive against EP2 or are prepared as monoclonal antibodies reactive with EP2 using the technique of Kohler and Milstein, Nature 256: 495–497 (1975). Monospecific antibody as used herein is defined as a single antibody species or multiple antibody species with homogenous binding characteristics for EP2. Homogenous binding as used herein refers to the ability of the antibody species to bind to a specific antigen or epitope, such as those associated with the EP2, as described above. EP2 specific antibodies are raised by immunizing animals such as mice, rats, guinea pigs, rabbits, goats, horses and the like, with an appropriate concentration of EP2 or a peptide derived from the sequence of the EP2 protein either with or without an immune adjuvant.

Preimmune serum is collected prior to the first immunization. Each animal receives between about 0.1 µg and about 1000 µg of EP2 or EP2-related peptide associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consisted of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of EP2 or EP2-related peptide in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with EP2 or a peptide derived from the sequence of the EP2 protein are prepared by immunizing inbred mice, preferably Balb/c, with EP2 or EP2-related peptide. The mice are immunized by the IP or SC route with about 1 µg to about 100 µg, preferably about 10 µg, of EP2 or EP2-related peptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 µg of EP2 in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using EP2 or EP2-related peptide as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-EP2 mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of EP2 in body fluids or tissue and cell extracts.

It is readily apparent that the above described methods for producing monospecific antibodies may be utilized to produce antibodies specific for EP2 polypeptide fragments, or full-length EP2 polypeptide.

EP2 antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing such as detergents and the cell culture supernatants or cell extracts containing EP2 or EP2 fragments are slowly passed through the column. The column is then washed with phosphate buffered saline together with appropriate membrane solubilizing such as detergents until the optical density ($A_{280}$) falls to background, then the protein is eluted with 0.23M glycine-HCl (pH 2.6) together with appropriate membrane solubilizing such as detergents. The purified EP2 protein is then dialyzed against phosphate buffered saline together with appropriate membrane solubilizing agent, such as detergents.

One method suitable for the isolation of DNA encoding the prostaglandin receptor of the present invention involves the utilization of amino acid and/or DNA sequence information obtained from other G-protein-linked receptors. Since other prostaglandin receptors are known to be G-protein linked, certain regions or domains such as the transmembrane and/or cytoplasmic domains, are expected to have some degree of homology sufficient to produce a probe for the isolation of novel receptors.

Prostaglandins and leukotrienes are known to transduce their signals via G-protein-linked receptors. Distinct receptors for $PGH_2$/thromboxane $A_2$, $PGI_2$, $PGE_2$, $PGD_2$, $PGF2\alpha$, $LTB_4$, and $LTD_4$ present in various tissues have been described. Some of the receptors have been solubilized and partially purified (Dutta-Roy, A. K. et al., (1987) JBC, 262, pp. 12685; Tsai, A. L. et al., (1989), JBC, 264, pp 61; 168—Watanabe, T. et. al., (1990), JBC, 265, pp. 21237) and the human platelet $TXA_2$ receptor has been purified to apparent homogeneity (Ushikubi, F. et. al., (1989), JBC, 264, pp. 16496). The purified thromboxane receptor exhibited a very broad band on a SDS-polyacrylamide gel centered at appr. 57 kDa. Enough protein was obtained for partial sequence information.

An approach to the isolation of other eicosanoid receptor genes by homology screening was taken, with the assumption that these receptors are related in primary structure (Sugimoto, Y. et al., (1992), JBC, 267, pp. 6463). Since these receptors are of the G-protein-coupled receptor superfamily there are areas of homology which are likely to be found in the transmembrane region and in the cytoplasmic domains. Therefore, various known G-protein linked receptors related to the prostaglandin receptors may be utilized to provide DNA probes to regions of the receptor protein-encoding DNA sought, which is likely to have homology, such as the transmembrane region.

Using a 0.68-kb fragment of a mouse EP2 receptor cDNA which encodes the c-terminal 165 amino acid region of this receptor was used to screen a human lung library from which a full-length human EP2 cDNA was isolated. This 1.958 kb cDNA clone encodes a 488-amino acid protein. This protein was designated as the EP2 receptor. Like many other G-protein coupled receptors the EP2 receptor shares several common features. Firstly, there are 2 potential N-linked glycosylation sites at Asn7 and Asn177 in the putative extracellular amino terminus. Secondly, conserved cysteine residues are found in extracellular loops 1 and 2. There are multiple serine residues, potential sites of protein kinase phosphorylation, throughout the C-terminus and third cytoplasmic loops. The EP2 receptor does not contain an aspartic acid residue in transmembrane three which is characteristic of the receptors binding cationic amino-containing ligands, however, it possesses a conserved arginine (position 315) found in all known eicosanoid receptors within transmembrane seven. This region is the most highly conserved among the eicosanoid receptors.

The novel prostaglandin receptor of the present invention is suitable for use in an assay procedure for the identification of compounds which modulate the receptor activity. Modulating receptor activity, as described herein includes the inhibition or activation of the receptor and also includes directly or indirectly affecting the normal regulation of the receptor activity. Compounds which modulate the receptor activity include agonists, antagonists and compounds which directly or indirectly affect regulation of the receptor activity.

The prostaglandin receptor of the present invention may be obtained from both native and recombinant sources for use in an assay procedure to identify receptor modulators. In general, an assay procedure to identify prostaglandin receptor modulators will contain the prostaglandin receptor of the present invention, and a test compound or sample which contains a putative prostaglandin receptor modulator. The test compounds or samples may be tested directly on, for example, purified receptor protein whether native or recombinant, subcellular fractions of receptor-producing cells whether native or recombinant, and/or whole cells expressing the receptor whether native or recombinant. The test compound or sample may be added to the receptor in the presence or absence of a known labelled or unlabelled receptor ligand. The modulating activity of the test compound or sample may be determined by, for example, analyzing the ability of the test compound or sample to bind to the receptor, activate the receptor, inhibit receptor activity, inhibit or enhance the binding of other compounds to the receptor, modify receptor regulation, or modify an intracellular activity.

The identification of modulators of EP2 receptor activity are useful in treating disease states involving the EP2 receptor activity. Other compounds may be useful for stimulating or inhibiting activity of the receptor. Selective agonists or antagonists of the EP2 receptor may be of use in the treatment of edema associated with inflammation, pain response and fever, and may have utility as modulators of osteoclast function and hence bone resorbtion, T and B-lymphocyte function, and hence immunilogical reactions, smooth muscle relaxation, including the varcular and trachiobronchial networks, and neoplastic and metastatic tumor growth. The isolation and purification of an EP2-encoding DNA molecule would be useful for establishing the tissue distribution of EP2 receptors, studying changes in EP2 receptor expression in disease states, as well as establishing a process for identifying compounds which modulate EP2 receptor activity.

The following examples are provided for the purpose of illustrating the present invention without, however, limiting the same thereto.

EXAMPLE 1

Cloning of the EP2 cDNA

A mouse EP2 partial cDNA (680 bp) was obtained by RT-PCR from mouse mastocytoma P-815 cell total RNA and cloned. This mouse EP2 fragment was used to generate a $^{32}$P-labeled cDNA probe to screen a human lung lambda gt10 library (Clontech, Palo Alto, Calif.) using standard techniques (Sambrook et al., 1989, Molecular Cloning: A Laboratory Manual, 2nd Ed., Cold Spring Harbor Laboratory, Cold Spring Harbor, N.Y.).

From this screening a 1.958 kb cDNA clone was plaque-purified and DNA was prepared by the plate lysate method (Sambrook et al., 1989, Molecular Cloning: A Laboratory Manual, 2nd Ed., Cold Spring Harbor Laboratory, Cold Spring Harbor, N.Y.).

Subcloning and sequencing of cDNA

The 1.958 kb EcoRI fragment (EP2) was subcloned into pSK vector (Stratagene, La Jolla, Calif.) for sequencing using the T7 DNA polymerase sequencing kit (Pharmacia). The DNA was sequenced entirely on both strands using the KS and SK primers (Stratagene, La Jolla, Calif.) or primers generated from the determined sequence. The nucleotide sequence of EP2 is shown in Table 1. The amino acid sequence for the encoded protein is shown in Table 2. The 1.958 kb fragment (EP2; FIG. 1), when sequenced, was found to contain sequence homology to the human EP1, EP3 and thromboxane receptor cDNA and the putative heptahelical arrangement characteristic of G protein-coupled receptors was evident. A long open reading frame (1464 bp) was determined which would result in a 488 amino acid polypeptide with a predicted relative molecular mass of 53,115. The ATG assigned as the initiator codon matches the Kozak consensus sequence for translation initiation (Kozak, 1989 J. Cell. Biol., 108, pp 229–241). There are 388 bp of 5'-untranslated sequence including an in frame TGA stop codon 86 bp upstream of the predicted start codon.

EXAMPLE 2

Construction of pcDNAIamp-EP2 expression vector

The 1.507 Kb Fsp1-Sca1 human EP2 cDNA fragment was subcloned into the EcoRV site of pcDNAIamp and the correct orientation was verified by Pst I digestion.

TABLE 1

CGGCACAGCCTCACACCTGAACGCTGTCCTCCCGCAGACGAGACCGGCGGGCACTGCAAA
GCTGGGACTCGTCTTTGAAGGAAAAAAAATAGCGAGTAAGAAATCCAGCACCATTCTTCA
CTGACCCATCCCGCTGCACCTCTTGTTTCCCAAGTTTTTGAAAGCTGGCAACTCTGACCT
CGGTGTCCAAAAATCGACAGCCACTGAGACCGGCTTTGAGAAGCCGAAGATTTGGCAGTT
TCCAGACTGAGCAGGACAAGGTGAAAGCAGGTTGGAGGCGGGTCCAGGACATCTGAGGGC
TGACCCTGGGGGCTCGTGAGGCTGCCACCGCTGCTGCCGCTACAGACCCAGCCTTGCACT
CCAAGGCTGCGCACCGCCAGCCACTATCATGTCCACTCCCGGGGTCAATTCGTCCGCCTC
CTTGAGCCCCGACCGGCTGAACAGCCCAGTGACCATCCCGGCGGTGATGTTCATCTTCGG
GGTGGTGGGCAACCTGGTGGCCATCGTGGTGCTGTGCAAGTCGCGCAAGGAGCAGAAGGA
GACGACCTTCTACACGCTGGTATGTGGGCTGGCTGTCACCGACCTGTTGGGCACTTTGTT
GGTGAGCCCGGTGACCATCGCCACGTACATGAAGGGCCAATGGCCCGGGGGCCAGCCGCT
GTGCGAGTACAGCACCTTCATTCTGCTCTTCTTCAGCCTGTCCGGCCTCAGCATCATCTG
CGCCATGAGTGTCGAGCGCTACCTGGCCATCAACCATGCCTATTTCTACAGCCACTACGT
GGACAAGCGATTGGCGGGCCTCACGCTCTTTGCAGTCTATGCGTCCAACGTGCTCTTTTG
CGCGCTGCCCAACATGGGTCTCGGTAGCTCGCGGCTGCAGTACCCAGACACCTGGTGCTT
CATCGACTGGACCACCAACGTGACGGCGCACGCCGCCTACTCCTACATGTACGCGGGCTT
CAGCTCCTTCCTCATTCTCGCCACCGTCCTCTGCAACGTGCTTGTGTGCGGCGCGCTGCT
CCGCATGCACCGCCAGTTCATGCGCCGCACCTCGCTGGGCACCGAGCAGCACCACGCGGC
CGCGGCCGCCTCGGTTGCCTCCCGGGGCCACCCCGCTGCCTCCCCAGCCTTGCCGCGCCT
CAGCGACTTTCGGCGCCGCCGGAGCTTCCGCCGCATCGCGGGCGCCGAGATCCAGATGGT
CATCTTACTCATTGCCACCTCCCTGGTGGTGCTCATCTGCTCCATCCCGCTCGTGGTGCG
AGTATTCGTCAACCAGTTATATCAGCCAAGTTTGGAGCGAGAAGTCAGTAAAAATCCAGA
TTTGCAGGCCATCCGAATTGCTTCTGTGAACCCCATCCTAGACCCCTGGATATATATCCT
CCTGAGAAAGACAGTGCTCAGTAAAGCAATAGAGAAGATCAAATGCCTCTTCTGCCGCAT
TGGCGGGTCCCGCAGGGAGCGCTCCGGACAGCACTGCTCAGACAGTCAAAGGACATCTTC
TGCCATGTCAGGCCACTCTCGCTCCTTCATCTCCCGGGAGCTGAAGGAGATCAGCAGTAC
ATCTCAGACCCTCCTGCCAGACCTCTCACTGCCAGACCTCAGTGAAAATGGCCTTGGAGG
CAGGAATTTGCTTCCAGGTGTGCCTGGCATGGGCCTGGCCCAGGAAGACACCACCTCACT
GAGGACTTTGCGAATATCAGAGACCTCAGACTCTTCACAGGGTCAGGACTCAGAGAGTGT
CTTACTGGTGGATGAGGCTGGTGGGAGCGGCAGGGCTGGGCCTGCCCCTAAGGGGAGCTC
CCTGCAAGTCACATTTCCCAGTGAAACACTGAACTTATCAGAAAAATGTATATAATAGCC
AAGGAAAGAAATACAGTACTGTTTCTGGACCCTTATAAAATCCTGTGCAATAGACACATA
CATGTCACATTTAGCTGTGCTCAGAAGGGCTATCATCA (SEQ. ID. NO.: 1)

TABLE 2

MSTPGVNSSASLSPDRLNSPVTIPAVMFIFGVVGNLVAIVVLCKSRKEQKETTFYTLVCG
LAVTDLLGTLLVSPVTIATYMKGQWPGGQPLCEYSTFILLFFSLSGLSIICAMSVERYLA
INHAYFYSHYVDKRLAGLTLFAVYASNVLFCALPNMGLGSSRLQYPDTWCFIDWTTNVTA
HAAYSYMYAGFSSFLILATVLCNVLVCGALLRMHRQFMRRTSLGTEQHHAAAAASVASRG
HPAASPALPRLSDFRRRRSFRRIAGAEIQMVILLIATSLVVLICSIPLVVRVFVNQLYQP

TABLE 2-continued

SLEREVSKNPDLQAIRIASVNPILDPWIYILLRKTVLSKAIEKIKCLFCRIGGSRRERSG
QHCSDSQRTSSAMSGHSRSFISRELKEISSTSQTLLPDLSLPDLSENGLGGRNLLPGVPG
MGLAQEDTTSLRTLRISETSDSSQGQDSESVLLVDEAGGSGRAGPAPKGSSLQVTFPSET
LNLSEKCI   (SEQ. ID. NO.: 2)

EXAMPLE 3

Cloning of the EP2 cDNA into *E. coli* Expression Vectors

Recombinant EP2 is produced in *E. coli* following the transfer of the EP2 expression cassette into *E. coli* expression vectors, including but not limited to, the pET series (Novagen). The pET vectors place EP2 expression under control of the tightly regulated bacteriophage T7 promoter. Following transfer of this construct into an *E. coli* host which contains a chromosomal copy of the T7 RNA polymerase gene driven by the inducible lac promoter, expression of EP2 is induced when an appropriate lac substrate (IPTG) is added to the culture. The levels of expressed EP2 are determined by the assays described above.

The cDNA encoding the entire open reading frame for EP2 is inserted into the NdeI site of pET 11a. Constructs in the positive orientation are identified by sequence analysis and used to transform the expression host strain BL21. Transformants are then used to inoculate cultures for the production of EP2 protein. Cultures may be grown in M9 or ZB media, whose formulation is known in the art. After growth to an approximate $OD_{600}=1.5$, expression of EP2 is induced with 1 mM IPTG for 3 hours at 37° C. EP2 receptor binding activity will be found in membrane fractions from these cells.

EXAMPLE 4

In Vivo Translation of Synthetic EP2 mRNA by Xenopus Oocyte Microinjection and Expression in Mammalian Cells EP2 cDNA constructs are ligated into in vitro transcription vectors (the pGEM series, Promega) for the production of synthetic mRNAs.

Synthetic mRNA is produced in sufficient quantity in vitro by cloning double stranded DNA encoding EP2 mRNA into a plasmid vector containing a bacteriophage promoter, linearizing the plasmid vector containing the cloned EP2-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded EP2-encoding DNA is cloned into the bacteriophage promoter containing vector in the proper orientation using one or more of the available restriction endonuclease cloning sites on the vector which are convenient and appropriate for cloning EP2 DNA. The vector with the ligated EP2 DNA is used to transform bacteria, and clonal isolates are analyzed for the presence of the vector with the EP2 DNA in the proper orientation.

Once a vector containing the EP2-encoding DNA in the proper orientation is identified and isolated, it is linearized by cleavage with a restriction endonuclease at a site downstream from, and without disrupting, the EP2 transcription unit. The linearized plasmid is isolated and purified, and used as a template for in vitro transcription of EP2 mRNA.

The template DNA is then mixed with bacteriophage-specific DNA-dependent RNA polymerase in a reaction mixture which allows transcription of the DNA template forming EP2 mRNA. Several bacteriophage-specific DNA-dependent RNA polymerases are available, including but not limited to T3, T7, and SP6 RNA polymerase. The synthetic EP2 mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5'terminus of the mRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified EP2 mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic EP2 mRNA to produce EP2 protein. The microinjected oocytes are incubated to allow translation of the EP2 mRNA, forming EP2 protein.

These synthetic mRNAs are injected into Xenopus oocytes (stage 5–6) by standard procedures [Gurdon, J. B. and Wickens, M. D. Methods in Enzymol. 101:370–386, (1983)]. Oocytes are harvested and analyzed for EP2 expression as described below.

EXAMPLE 5 pcDNAIamp-EP2 expression in Xenopus oocytes

Oocytes were taken from adult females of *Xenopus laevis* using standard surgical procedure (Colman, A., 1984 In: Transcription and Translation—A Practical Approach, IRL Press). To remove follicle cells, oocytes were treated for 2–3 h with freshly made collagenase (2 mg/ml, type 2, Worthington Biochemical Corp., Freehold, N.J.) in $Ca^{2+}$-free ND96 solution (ND96 in mM: NaCl 96, KCl 2, $MgCl_2$ 1, HEPES 5, Na-pyruvate 2.5, theophylline 0.5 gentamicin 50 mg/ml, +1.8 $CaCl_2$, pH 7.6). Defolliculated stage 5–6 oocytes were selected and maintained in ND96 solution. Oocyte nuclei were injected with 1.6 ng of pcDNAIamp-EP2 plus 2.5 ng of pcDNAIamp-CFTR and then incubated at 18° C. for 48 h before challenge with agonist. CFTR (cystic fibrosis transmembrane regulator, a cAMP dependent Cl⁻ channel) was co-expressed with EP2 receptor in these oocytes and served as a reporter of changes in intracellular cAMP levels. Functional activity was determined by measurement of PGE2-induced CFTR-mediated Cl⁻ current. An oocyte was placed in a 0.5 ml perfusion chamber and voltage clamped at −60 mV (with microelectrodes of 0.5–2.0 MW resistance filled with 3M KCl) using a Turbo TEC01C amplifier (NP1 Instruments, Germany). Ligand-containing solution was perfused and the current response was recorded.

Figure 3:
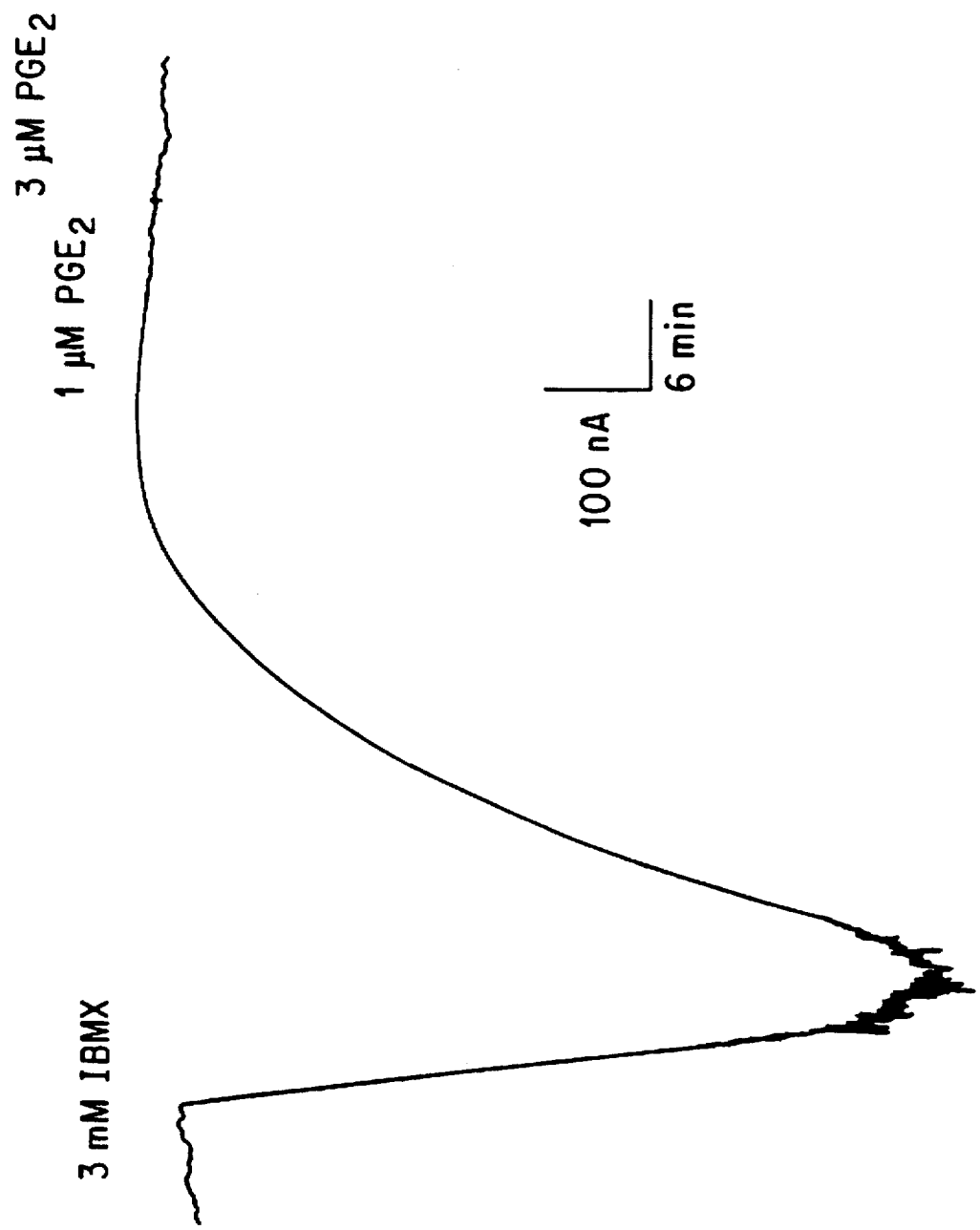
FIG. 3—IBMX-induced, CFTR-mediated $Cl^-$ current in (CFTR+anti-sense hEP2) cDNA injected oocytes is shown, noting the lack of response to 1 μM and 3 μM PGE2.
Figure 4A:
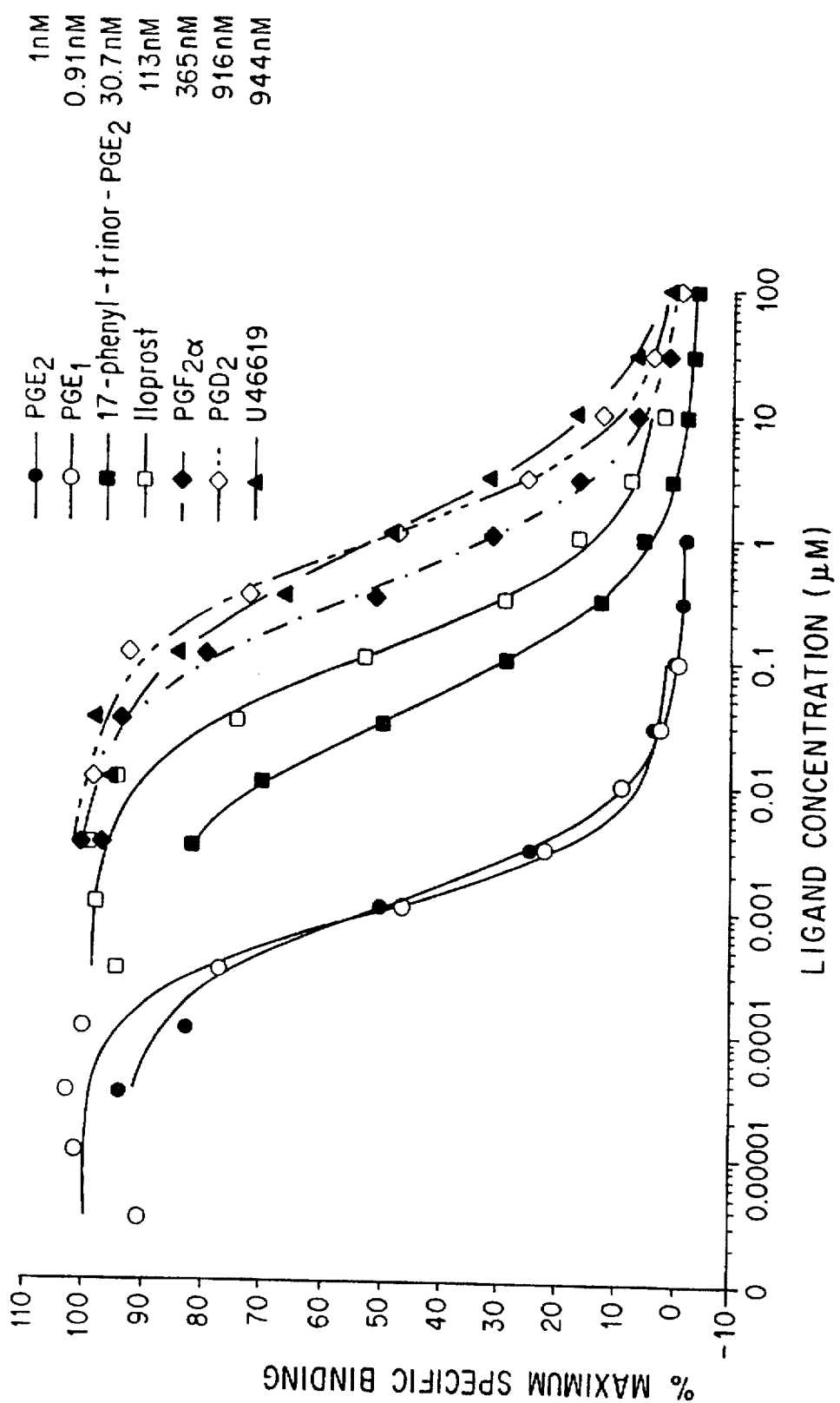
FIGS. 4A and B—Competition for [$^3$H]PGE2 specific binding to pcDNAIamp-hEP2 transfected COS-M6 membranes is shown by [$^3$H]PGE2 binding assays performed in the presence of: Panel A) 10 pM–10 mM PGE2 (l), PGE1 (o), 17-pheyyl-trinor PGE2 (n), iloprost (q), PGF2α (u), $PGD_2$ (◊), and U46619 (s) and Panel B. 100 pM–100 uM MB28767 (l), misoprostol (o), butaprost (n), AH6809 (q) and SC19220 (u).
Figure 4B:
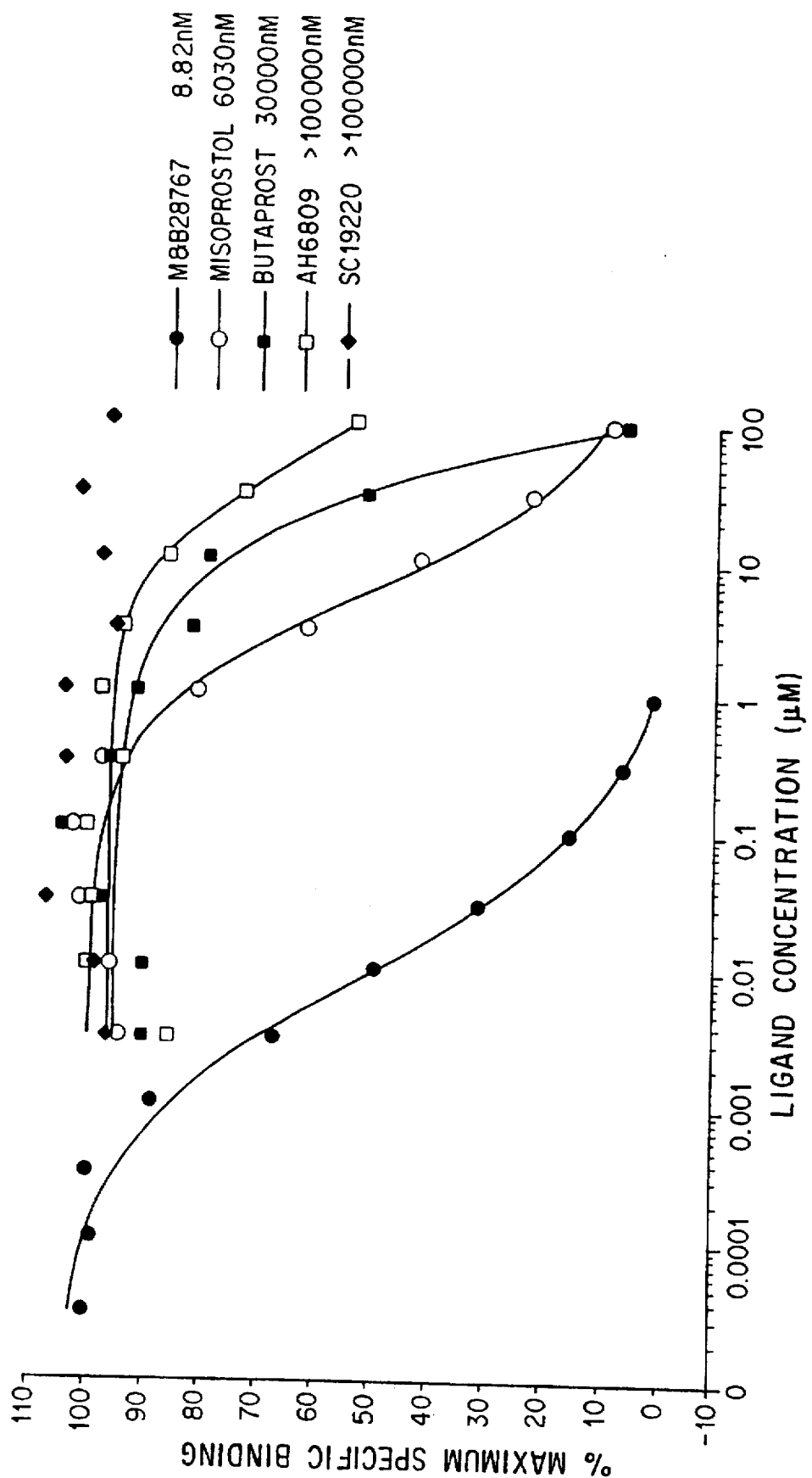

Perfusion of 1 nM PGE2 agonist, resulted in prominent current responses in oocytes injected with pcDNAIamp-EP2 plus pcDNAIamp-CFTR confirming that this clone encodes a functional EP2 receptor that is coupled to the cAMP signalling pathway (FIG. 3). The response to 1 μM $PGF_{2\alpha}$ was much smaller as expected for the EP2 receptor subtype. Such responses were absent in control (CFTR alone or CFTR plus antisense EP2 cDNA injected) oocytes (FIG. 4). This rank order of potency is consistent with that reported for the EP2 receptor [Coleman, et al., 1991].

EXAMPLE 6

Cloning of EP2 cDNA into a Mammalian Expression Vector

EP2 cDNA expression cassettes are ligated at appropriate restriction endonuclease sites to the following vectors containing strong, universal mammalian promoters: pBC12BI [Cullen, B. R. Methods in Enzymol. 152: 684–704 1988], and pEE12 (CellTech EP O 338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci USA 80: 2495–2499 [1983]) driven by the SV40 early promoter. An SV40 polyadenylation sequence is generated by a PCR reaction defined by primers 13978-120 and 139778-121 using pD5 (Berker and Sharp, Nucl. Acid Res. 13: 841–857 [1985]) as template. The resulting 0.25 Kb PCR product is digested with ClaI and SpeI and ligated into the 6.7 Kb fragment of pEE 12 which had been likewise digested. The resultant plasmid is digested with BglII and SfiI to liberate the 3' portion of the SV40 early promoter and the GScDNA from the vector. A 0.73 Kb SfiI-XhoII fragment isolated from plasmid pFR400 (Simonsen, C. C. and Levinson, A. D. Proc. Natl. Acad. Sci USA 80: 2495–2499 [1983]) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973 [1986]) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promoterless DNA fragment to generate the vector pSZ9016- 1.

Cassettes containing the EP2 cDNA in the positive orientation with respect to the promoter are ligated into appropriate restriction sites 3' of the promoter and identified by restriction site mapping and/or sequencing. These cDNA expression vectors are introduced into various host cells including, but not limited to: COS-7 (ATCC# CRL1651), CV-1 [Sackevitz et al., Science 238: 1575 (1987)], 293, L cells (ATCC# CRL6362)] by standard methods including but not limited to electroporation, or chemical procedures (cationic liposomes, DEAE dextran, calcium phosphate). Transfected cells and cell culture extracts can be harvested and analyzed for EP2 expression as described below.

All of the vectors used for mammalian transient expression can be used to establish stable cell lines expressing EP2. Unaltered EP2 cDNA constructs cloned into expression vectors will be expected to program host cells to make intracellular EP2 protein. The transfection host cells include, but are not limited to, CV-1 [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing EP2 cDNA with a drug selection plasmid including, but not limited to G418, aminoglycoside phosphotransferase, pLNCX [Miller, A. D. and Rosman G. J. Biotech News 7: 980–990 (1989)]; hygromycin, hygromycin-B phosphotransferase, pLG90 [Gritz, L. and Davies, J., GENE 25: 179 (1983)]; APRT, xanthine-guanine phosphoribosyl-transferase, pMAM (Clontech) [Murray, et al., Gene 31: 233 (1984)] will allow for the selection of stably transfected clones. Levels of EP2 are quantitated by the assays described above.

EP2 cDNA constructs are ligated into vectors containing amplifiable drug-resistance markers for the production of mammalian cell clones synthesizing the highest possible levels of EP2. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. USA 80: 2495 (1983)], transfected into DHFR-CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thymidine kinase gene [Colbere and Garopin, F., Proc. Natl. Acad. Sci. 76: 3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 7

Expression of the EP2 receptor in COS-M6 cells and [³H]PGE2 binding assays

The recently cloned human prostaglandin E2 (EP2) receptor was subcloned into the pcDNAIamp plasmid (Invitrogen) and transfected into COS-M6 cells using the DEAE-dextran method. The cells were maintained in culture for 72 h, then harvested and membranes prepared by differential centrifugation (1000×g for 10 min, then 100,000×g for 30 min) following lysis of the cells by nitrogen cavitation. [³H] Prostaglandin E2 ([³H]PGE2) binding assays were performed in 10 mM MES/KOH pH 6.0, containing 1.0 mM EDTA, 10 mM $MnCl_2$, 0.3 nM [³H]PGE2 and 12–15 μg of protein from the 100,000×g membrane fraction. Incubations were conducted for 45 min at 30° C. prior to separation of the bound and free radioligand by rapid filtration through Whatman GF/B filters presoaked at 4° C. in washing buffer (10 µM MES/KOH (pH 6.0) containing 0.01% bovine serum albumin). The filters were washed with approximately 16 ml of washing buffer and the residual [$^3$H]PGE2 bound to the filter was quantified by liquid scintillation counting. Specific binding was defined as the difference between total binding and non-specific binding, determined in the presence of 2 µM PGE2.

The cloned human EP2 receptor was transfected into COS-M6 cells and [$^3$H]PGE2 binding assays were performed with membranes prepared from the transfected cells. In competition assays PGE2 and PGE1 were the most potent competing ligands with IC50 values of 1 nM (FIG. 5). The rank order of potency for prostaglandins and related analogs was: PGE2=PGE1>>phenyl-trinor PGE2>iloprost>PGF$_{2\alpha}$>PGD$_2$≈U46619. U46619 and iloprost are stable analogs of thromboxane and prostacyclin and display comparable potency at the TP and IP receptors, respectively. In addition, the EP3 agonist MB28767 was approximately 30-fold less potent at EP2 than EP3, the EP1 antagonist AH6809 and SC19220 were essentially inactive at EP2 and butaprost, an EP2 agonist was also relatively inactive with an IC$_{50}$ of 30 µM. Misoprostol, a gastrointestinal protective agent had an IC$_{50}$ of 6.03 µM. This rank order of potency has been predicted for the EP2 receptor from previous pharmacological studies.

EXAMPLE 8

Cloning of EP2 cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing EP2 cDNA are produced by the following standard methods (In Vitrogen Maxbac Manual): the EP2 cDNA constructs are ligated downstream of the polyhedrin promoter in a variety of baculovirus transfer vectors, including the pAC360 and the pBlueBac vector (In Vitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of β-galactosidase expression (Vialard, et al. 1990, J. Virol., 64, pp 37–50). Following plaque purification and infection of sf9 cells with EP2 recombinant baculovirus, EP2 expression is measured by the assays described above.

The cDNA encoding the entire open reading frame for EP2 is inserted into the BamHI site of pBlueBacII. Constructs in the positive orientation with respect to the polyhedrin promoter are identified by sequence analysis and used to transfect Sf9 cells in the presence of linear AcNPV wild type DNA.

Authentic, active EP2 is found associated with the membranes of infected cells. Membrane preparations are prepared from infected cells by standard procedures.

EXAMPLE 9

Cloning of EP2 cDNA into a yeast expression vector

Recombinant EP2 is produced in the yeast S. cerevisiae following the insertion of the optimal EP2 cDNA construct into expression vectors designed to direct the intracellular expression of heterologous proteins. For intracellular expression, vectors such as EmBLyex4 or the like are ligated to the EP2 cistron [Rinas, U. et al., Biotechnology 8: 543–545 (1990); Horowitz B. et al., J. Biol. Chem. 265: 4189–4192 (1989)]. The levels of expressed EP2 are determined by the assays described above.

EXAMPLE 10

Purification of Recombinant EP2

Recombinantly produced EP2 may be purified by antibody affinity chromatography.

EP2 antibody affinity columns are made by adding the anti-EP2 antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized EP2 is slowly passed through the column. The column is then washed with phosphate-buffered saline together with detergents until the optical density (A280) falls to background, then the protein is eluted with 0.23M glycine-HCl (pH 2.6) together with detergents. The purified EP2 protein is then dialyzed against phosphate buffered saline together with detergents.

---

What is claimed is:

1. An isolated and purified prostaglandin receptor protein wherein said protein comprises the amino acid sequence

MSTPGVNSSASLSPDRLNSPVTIPAVMFIF

GVVGNLVAIVVLCKSRKEQKETTFYTLVCG

LAVTDLLGTLLVSPVTIATYMKGQWPGGQP

LCEYSTFILLFFSLSGLSIICAMSVERYLA

INHAYFYSHYVDKRLAGLTLFAVYASNVLF

CALPNMGLGSSRLQYPDTWCFIDWTTNVTA

HAAYSYMYAGFSSFLILATVLCNVLVCGAL

LRMHRQFMRRTSLGTEQHHAAAAASVASRG

HPAASPALPRLSDFRRRRSFRRIAGAEIQM

VILLIATSLVVLICSIPLVVRVFVNQLYQP

SLEREVSKNPDLQAIRIASVNPILDPWIYI

ILRKTVLSKAIEKIKCLFCRIGGSRRERSG

QHCSDSQRTSSAMSGHSRSFISRELKEISS

TSQTLLPDLSLPDLSENGLGGRNLLPGVPG

MGLAQEDTTSLRTLRISETSDSSQGQDSES

VLLVDEAGGSGRAGPAPKGSSLQVTFPSET

LNLSEKCI (SEQ.ID.NO.:2).

2. A method of determining whether a test compound binds to a prostaglandin receptor, comprising:

(a) providing, mammalian host cells transfected with a nucleic acid encoding a prostaglandin receptor wherein said receptor comprises the amino acid sequence of claim 1;

(b) cultivating said mammalian host cells under conditions such that said receptor is expressed, (c) combining said test compound with said mammalian host cells or with membranes containing said prostaglandin receptor prepared from said mammalian host cells; and (d) determining whether said test compound binds to said prostaglandin receptor.

3. A method of determining whether a test compound is an agonist of a prostaglandin receptor, comprising:

(a) introducing a nucleic acid encoding a prostaglandin receptor comprising the amino acid sequence of claim 1 and a nucleic acid encoding the cystic fibrosis transmembrane regulator into Xenopus oocytes;

(b) cultivating said oocytes under conditions such that the prostaglandin receptor and the cystic fibrosis transmembrane regulator are expressed;

(c) combining the test compound with the oocytes of step (b);

(d) measuring the Cl$^-$ current in the oocytes following combination with the test compound;

where an increase in the Cl$^-$ current in the oocytes following combination with the test compound indicates that the test compound is an agonist of the prostaglandin receptor.

* * * * *